(12) United States Patent
Hogan (10) Patent No.: US 7,139,078 B2
(45) Date of Patent: Nov. 21, 2006

(54) HIGH RESOLUTION ANALYSIS SYSTEM (76) Inventor: Josh N. Hogan, 620 Kingswood Way, Los Altos, CA (US) 94022

( * ) Notice: Subject to any disclaimer, the term of this patent is extended or adjusted under 35 U.S.C. 154(b) by 309 days.

(21) Appl. No.: 10/895,610

(22) Filed: Jul. 21, 2004

(65) Prior Publication Data

US 2005/0018203 A1  Jan. 27, 2005

Related U.S. Application Data

(60) Provisional application No. 60/489,201, filed on Jul. 22, 2003.

(51) Int. Cl.
*G01B 9/02* (2006.01)

(52) U.S. Cl. .................................. 356/480; 356/450

(58) Field of Classification Search ................ 356/450, 356/451, 477, 479, 480, 484
See application file for complete search history.

(56) References Cited

U.S. PATENT DOCUMENTS

| | | | |
|---|---|---|---|
| 5,585,913 A * | 12/1996 | Hariharan et al. | 356/4.09 |
| 6,507,404 B1* | 1/2003 | Nishioki et al. | 356/450 |
| 6,522,911 B1* | 2/2003 | Toida et al. | 600/473 |
| 6,728,571 B1* | 4/2004 | Barbato | 600/478 |

* cited by examiner

*Primary Examiner*—Hwa(Andrew) Lee
*Assistant Examiner*—Michael A. Lyons (57) ABSTRACT

A high resolution sub-surface imaging and analysis system includes at least one repetitive, broad spectral width, optical signal generator. It further includes an optical processing system which provides a probe and a reference beam, applies the probe beam to the target to be analyzed, recombines the beams interferometrically and varies the coherence phase relationship of the two beams. It further includes electronic control and processing systems.

33 Claims, 7 Drawing Sheets

HIGH RESOLUTION ANALYSIS SYSTEM

CROSS REFERENCES TO RELATED APPLICATIONS

This application, docket number JH20030722, claims priority from provisional application, Ser. No. 60/489,201 filed on Jul. 22, 2003.

RELATED APPLICATIONS

This invention relates to utility application entitled "A Non-invasive Analysis System", Ser. No. 10/870,121 filed by Josh Hogan on Jul. 17, 2004, the contents of which are incorporated by reference as if fully set forth herein. This invention also relates to utility application entitled "A Real Time Imaging and Analysis System", Ser. No. 10/870,120 filed by Josh Hogan on Jul. 17, 2004, the contents of which are incorporated by reference as if fully set forth herein.

FIELD OF INVENTION

The invention relates to high resolution imaging and analysis and in particular to sub-surface imaging and analysis.

BACKGROUND OF THE INVENTION

In a typical imaging and analysis system a target (or sample) is scanned in two dimensions by a probe signal. A corresponding detected signal provides information about the scanned points in the target which can then be displayed as an image and analyzed visually or can be analyzed electronically by an electronic processing system.

Sub-surface imaging is a powerful technique for non-destructive imaging or quantitative analysis of a variety of targets (also referred to as samples) including, semiconductor wafers, materials, human tissue, etc. The analysis can include scanning for defects, discontinuities, or in the case of tissue, abnormalities such as malignant growths.

High resolution sub-surface imaging is particularly valuable in the case of in vivo analysis of human tissue, where, non-destructive, non-invasive sub-surface scanning allows convenient analysis of potentially abnormal tissue without the need for a costly, time consuming and invasive biopsy.

Two dimensional scanning of imaging systems typically consists of scanning in one dimension along one direction or axis then, at a lower speed, scanning or stepping in a direction orthogonal to the first direction. Scanning is typically accomplished by electro mechanical devices, such as galvanometers or moving coils actuators. Other scanning technologies include rotating polygons which are expensive, physically large and have significant alignment issues or acousto-optic (AO) scanners which are expensive, require significant RF power and, since the angular deviation is small, involve systems that are physically large.

A typical sub-surface imaging technology, such as confocal microscopy, can generate tomographic images, for example of tissue, containing information similar to biopsy sections, by scanning a one dimensional array, parallel to the surface of the tissue (x-scan), at varying depths (z-scan) in tissues. The series of one dimensional scans at various depths can be displayed as a single tomographic image. High resolution is achieved by having a high numerical aperture (NA) focusing lens. Such lenses have an undesirable trade off between working distance and physical size of the lens. To achieve both high resolution and long working distance require large and therefore very expensive lenses. These systems also typically have undesirable moving parts or expensive and high power consumption AO modulators.

Another sub-surface imaging technology, optical coherence tomography, can also generate tomographic, biopsy like images. Such systems use a Super-luminescence diode (SLD) as the optical source. The SLD output beam has a broad bandwidth and short coherence length. Optical coherence tomography involves splitting the output beam into a probe and reference beam. The probe beam is applied to the system to be imaged or analyzed (the target). Light scattered or reflected back from the target is combined with the reference beam to form the measurement signal.

Because of the short coherence length only light that is scattered or reflected from a depth within the target such that the total optical path lengths of the probe and reference are equal combine interferometrically. Thus the interferometric signal provides a measurement of the scattering or reflection value at a particular depth within the target. By varying the length of the reference path length, a measurement of the scattering values at various depths can be measured and in this manner, the z-axis can be scanned. The reference path length is typically varied by physically moving a reflecting mirror.

In this case, high resolution in one dimension is achieved by using an SLD with a broad wavelength range (or large spectral width). This is typically limited by the properties of the material comprising the SLD, which represents a limitation on the achievable resolution. Because z dimension scanning requires varying the path length, at least some of the above mentioned limitations, such as mechanical moving parts or expensive AO modulators, apply to this imaging method also and, in general, these limitations represent a barrier to applying current imaging technologies to compact, cost effective high resolution applications.

Furthermore, SLDs emit incoherent light that consists of amplified spontaneous emissions with associated wide angle beam divergence which have the undesirable beam handling and noise problems. The beam is also a continuous wave (CW) source with no opportunity for temporal based signal enhancement. Also, because of the random nature of spontaneous emission, the reference signal must be derived from same SLD signal and have equal optical path length as the probe signal. Therefore the relative optical path length must be physically changed by a scanning mechanism and the reference path length must be of similar magnitude to the probe path length. These aspects cause systems based on SLD sources have significantly lower signal to noise characteristics and present problems in practical high resolution implementations.

In general one or more of these aspects of high cost components, moving parts, high power consumption and large physical size make existing imaging systems unsuitable for cost effective, compact, robust, high resolution imaging systems. There is therefore an unmet need for a cost effective, compact, robust, high resolution sub-surface imaging or analysis system.

SUMMARY OF THE INVENTION

The invention is a method apparatus and system for a sub-surface high resolution imaging and analysis system. The invention includes at least one repetitive, broad spectral width, optical signal generator. It further includes an optical processing system which provides a probe and a reference beam, applies the probe beam to the target to be analyzed, recombines the beams interferometrically and varies the relative temporal relationship of the coherence phase of the two beams. It further includes electronic control and processing systems.

DETAILED DESCRIPTION OF THE INVENTION

Imaging and analysis systems based on optical coherence tomography employ an optical source that consists of a broad band of incoherent wavelengths, generated by amplifying stimulated emission, with the problems and limitations described above. An alternative approach, which addresses these problems and limitations, is to use a source having a broad set of discrete coherent wavelengths. A preferred embodiment of this invention is illustrated in and described with reference to FIG. 1 where a high resolution optical imaging and analysis system is shown.

Figure 1:
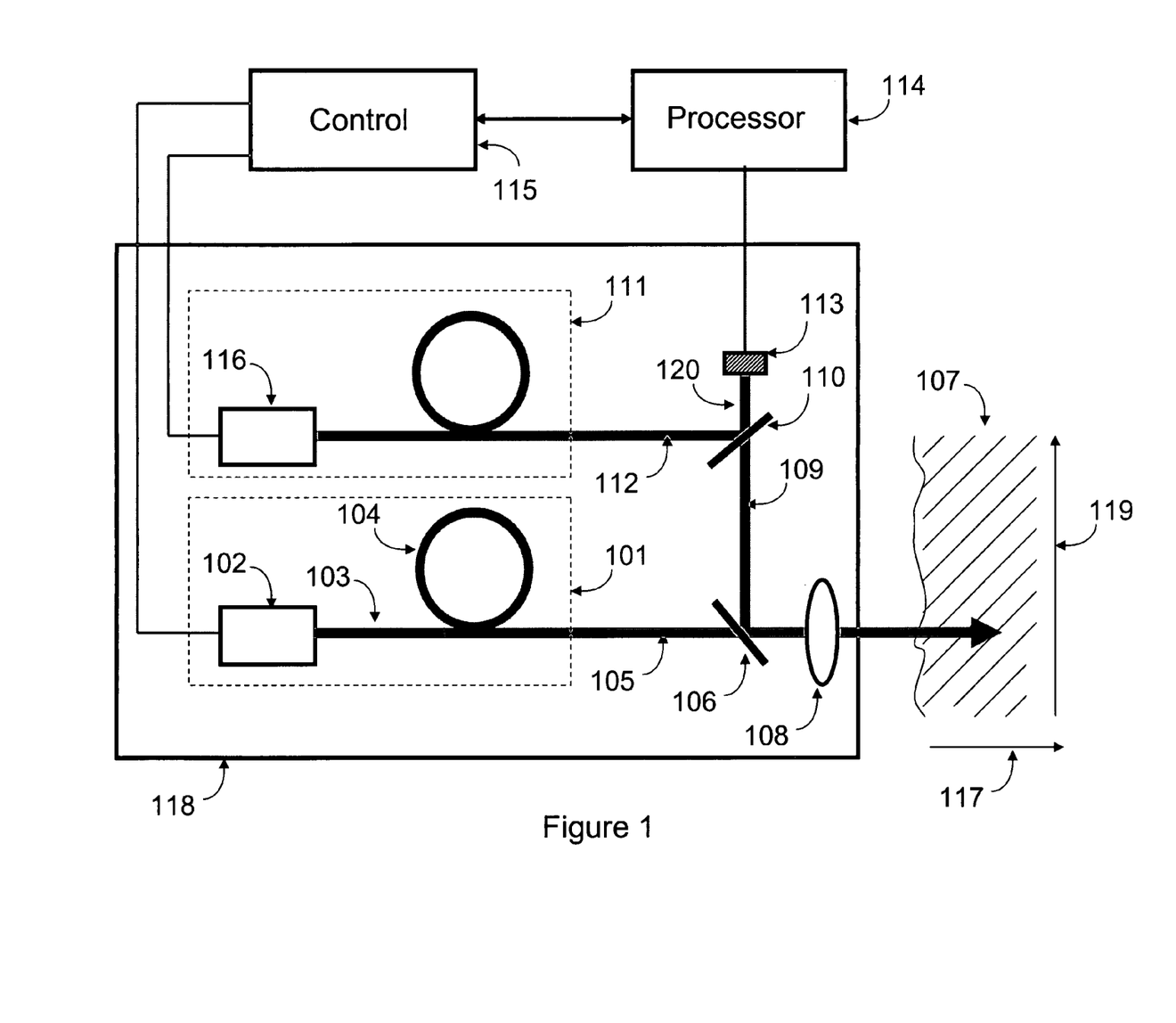
FIG. 1 is an illustration of the high resolution analysis system according to the invention.

The system described in this preferred embodiment includes a first pulsed optical source 101 which includes a first pulsed laser source, which in the preferred embodiment is a mode locked laser diode 102, whose output 103, consists of a first set of wavelengths or modes, that have a repetitive phase relationship with each other. The output 103 is referred to as a first repetitive optical signal and is coupled by means of a wave guide to micro ring resonator 104 which has the effect of broadening the spectral width of the first repetitive optical signal. The micro ring resonator consists of highly non linear material which redistributes the optical energy in the first repetitive optical signal to a broad band of wavelengths. This output 105 from the pulsed optical source is herein referred to as a first broadened optical signal.

The output 105, also referred to as a probe signal, is passed through a beam splitter 106 and applied to a target 107 through a focusing lens 108. This focusing lens may have a long Raleigh range of the order of a milli meter and may be movable to reposition the focal spot. At least part of the first broadened optical signal applied to the target to be analyzed 107 is returned from the target, by means of scattering or reflection, and captured by the lens 108. Scattering or reflection occurs because material properties of the target, or discontinuities due to defects or changes of refractive index. The captured returned broadened optical signal passes back to the beam splitter 106, where at least part of it 109 is directed to another beam splitter 110. The part of the captured returned signal directed at the beam splitter 110 is referred to as a returned optical signal 109.

A second pulsed optical source 111, (similar to the source 101) generates and spectrally broadens a second repetitive optical signal. The output 112 of the second pulsed optical source is a second broadened optical signal, referred to as a reference optical signal, is also applied to the beam splitter 110, where it is combined interferometrically with the returned optical signal 109. Combining the returned optical signal with the reference optical signal results in an interference signal which is only be interferometrically significant when pulses from the two pulsed optical sources overlap, which provides a method of discriminating the return signal from different depths within the target. By mode locking the second pulsed laser source with a different frequency than the first pulsed laser source, (or modifying the relative phase relationships) returned signals from different depths within the target are scanned through, at a scan frequency related to the difference in frequency. In general, modifying the coherence phase relationship between the returned optical signal and the reference optical signal allows detecting an interferometric signal from different depths within the target. Detecting and processing the interference signal between the returned optical signal and the reference optical signal at multiple coherence phase relationships provides a means of performing analysis of the target. High resolution analysis is enabled by the spectral broadening of the optical signals.

The resolution with which signals from different depths can be distinguished (or discriminated) is related to the spectral width of the optical signal applied. A broader spectral range provides greater resolution, enabling higher resolution analysis and imaging. Spectral broadening can be accomplished by means of mode locking, further broadening can be accomplished by means of coupling to the non linear micro ring and still further broadening by amplifying the mode locked signal prior to coupling to the non linear micro ring.

In the preferred embodiment, the resulting interference signal 120 is detected by an opto-electronic detector 113 and electronically processed by an electronic processing module 114. An electronic control module 115 controls the mode locked operation of the laser diodes 102 and 116 and also provides timing information to the processing module 114. The processing module combines this timing information with the detected interference signals to compute scattering or reflection profiles as a function of depth within the target to generate a one dimensional scan, which provides the information to perform one dimensional analysis of the target and can constitute a one dimensional image of the target in the direction indicated by 117, (also called a z-scan).

The optical components, enclosed by the box 118 in FIG. 1, do not involve any moving parts and can be assembled in a compact manner on an optical micro-bench enabling a simple electro-mechanical scanning mechanism in a direction 119 (the x-scan) orthogonal to the first scanning direction to perform two dimensional analysis of the target and to generate a two dimensional image of the target. Three dimensional analysis or imaging can be performed by also stepping the system enclosed in the box 118 in a direction orthogonal to the direction 119 and 117.

The control module 115, along with the processing module 114, process the computed scattering or reflection profiles as a function of depth, optionally with previously stored information, to perform analysis on, or generate an image of the target. The control module 115 may also store the processed, computed and determined information and control parameters in non-volatile memory for display, for further analysis and future operation.

Figure 2:
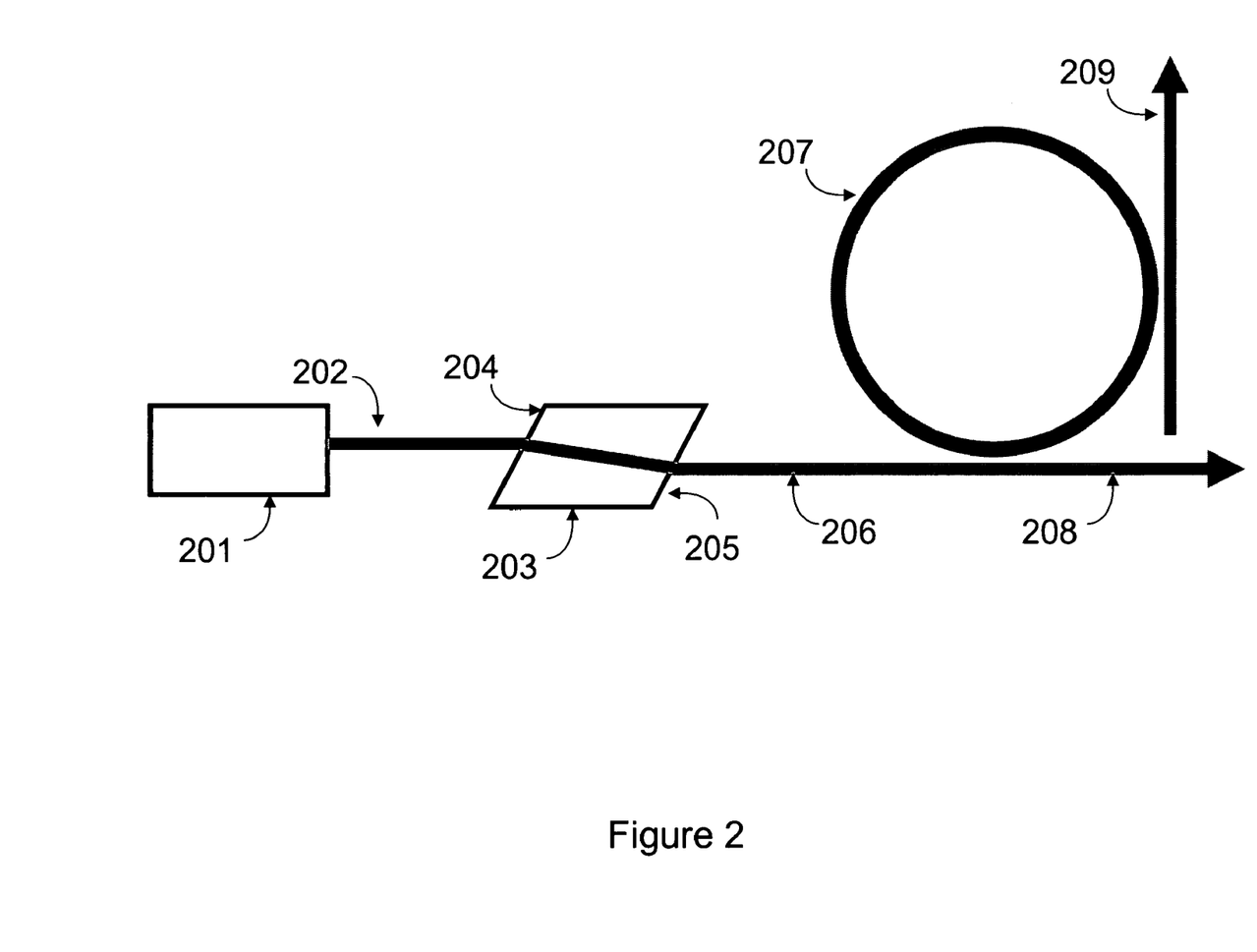
FIG. 2 is an illustration of a spectrally broadened mode locked laser source.

Alternative configurations of the pulsed laser sources 101 and 111 are illustrated in FIG. 2 where the output 202 of a mode locked laser diode 201 is (optionally) amplified by a semiconductor optical amplifier (SOA) 203, typically with angled facets 204 and 205 to minimize reflection issues. The amplified output 206 is coupled to a micro ring resonator 207 which redistributes the optical energy of the output 206 to a broader band of wavelengths. The broadened band of wavelengths may be out put on the same wave guide 208 as the input, or alternatively the broadened optical signal may be output by means of coupling to a different wave guide 209.

Figure 3A:
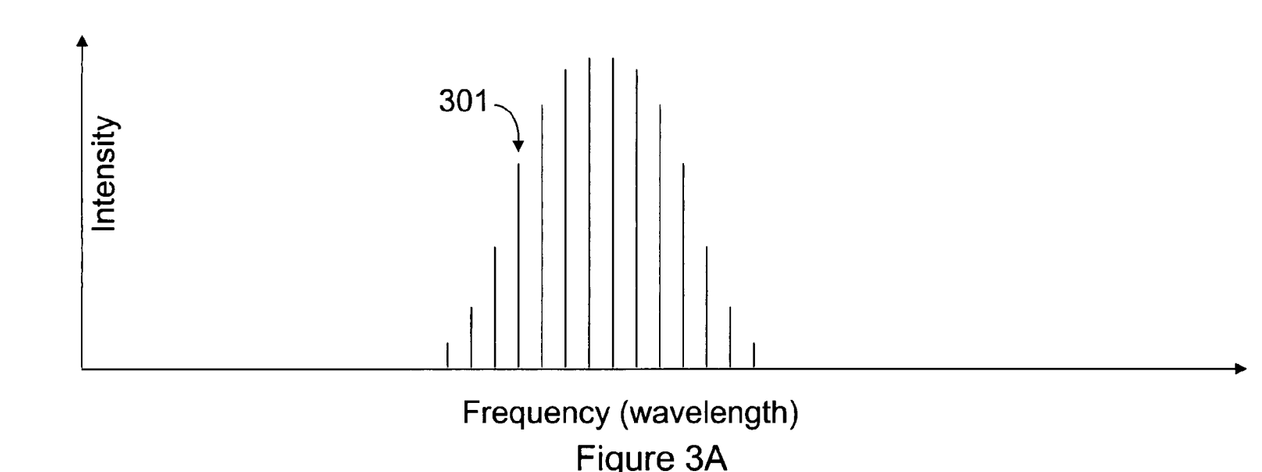
FIG. 3A is a frequency domain illustration of the output of mode locked laser optical source.
Figure 3B:
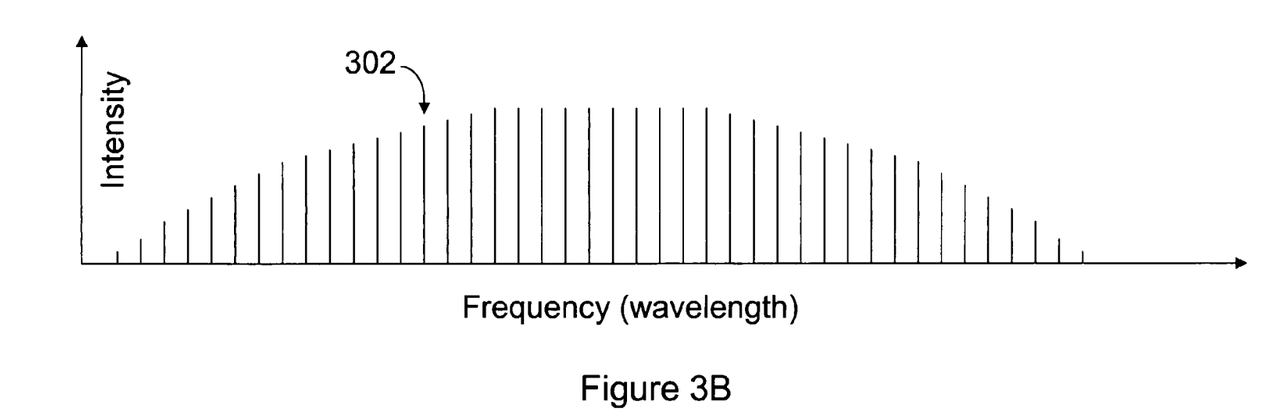
FIG. 3B is a frequency domain illustration of the output of spectrally broadened mode locked laser optical source.

The output of the mode locked laser 201 or the SOA 203 is illustrated in FIG. 3A which shows a set of wavelengths 301 evenly spaced in the frequency domain. The output of the micro ring resonator 208 or 209 is illustrated in FIG. 3A which shows a spectrally broadened set of wavelengths 302, also evenly spaced in the frequency domain.

Other alternative mode locked laser sources include mode locked lasers with spectral broadening accomplished by means of mode locking only or by addition of diffraction gratings. These can be either monolithic laser diode cavities with internal diffraction gratings designed to spectrally broaden and gain flattening the lasing medium, in either internal or external laser cavity configurations.

Mode locking can be accomplished electronically by applying an RF signal to a modulator or to the gain medium, or passively by means of a saturable absorber, such as a semiconductor saturable absorber, or by means of a semiconductor saturable absorber mirror, or by any combination of these techniques.

In alternative embodiments, the pulsed laser sources may consist of gain switched laser diodes, and may include an SOA, or may consist of a Q-switched laser. Spectral broadening may be accomplished by means of non-linear fiber, either in a resonant cavity configuration or in a single pass configuration.

Figure 4:
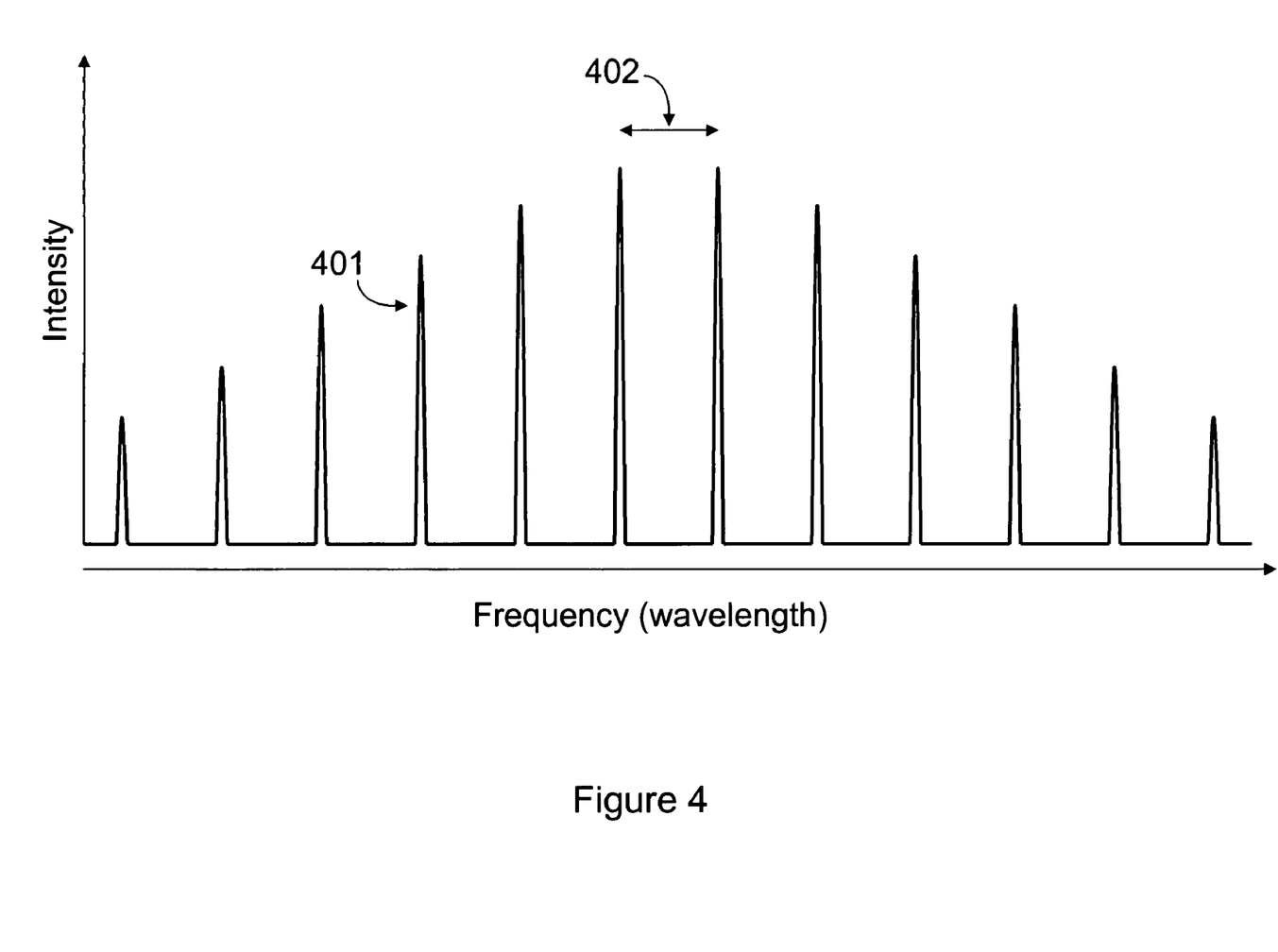
FIG. 4 is a frequency domain illustration of the output of a mode locked laser optical source.

The output of a mode locked laser diode is further illustrated in the frequency domain in FIG. 4 and consists of a set of modes, one of which is 401, which are separated from each other by a constant frequency difference 402. This frequency difference (delta_F) is related to the length of the laser diode according to the relationship delta_F=c/(2nL) where c is the speed of light, n is the refractive index of the lasing material and L is the length of the laser diode cavity.

Mode locking can be achieved by modulating the laser diode at a frequency equal to or harmonically related to the frequency delta_F. The output of the pulsed laser source 101, of FIG. 1, referred to as the probe signal, is illustrated in the time domain in FIG. 5, where it is shown as a pulse train 501 with a repetition period 503, (T1) which is the reciprocal of its repetition frequency delta_F1. The output of the second pulsed laser source 111, of FIG. 1, is shown as the pulse train 502 with a repetition period 504, (T2) which is the reciprocal of its frequency delta_F2.

Figure 5:
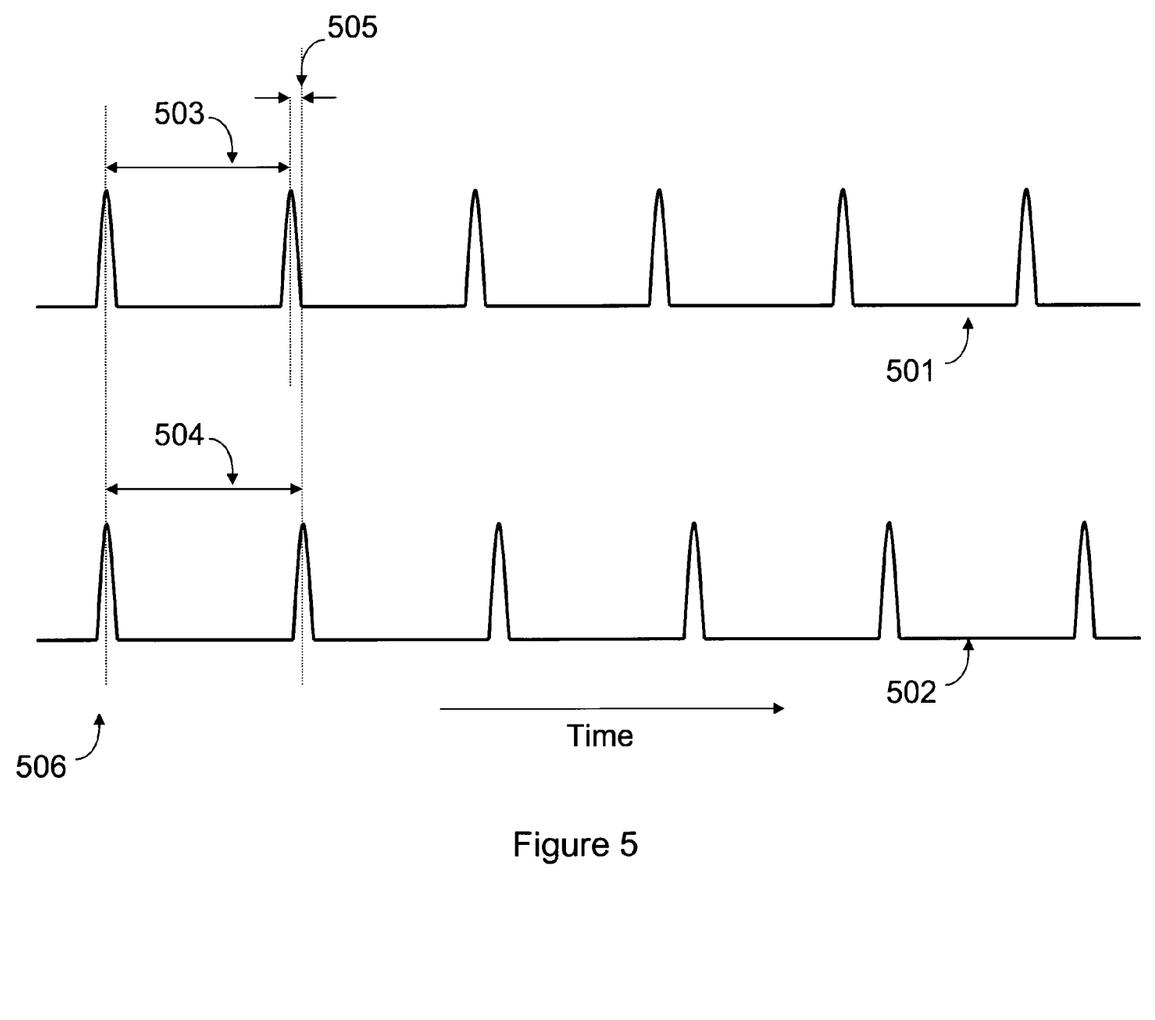
FIG. 5 is a time domain illustration of the outputs of two mode locked laser sources.

The difference between the two periods 505 corresponds to the difference between the two frequencies delta_F1 and delta_F2 and is referred to as a frequency offset. Pulses from the two pulse trains go from being aligned in time, as shown at point 506, to a systematic increase in misalignment until they come back into alignment. The frequency with which pulses come back into alignment is related to the frequency offset. The actual temporal relative alignment of the two pulse trains is referred to as their coherence phase offset.

When the returned optical signal 109 is combined with the reference optical signal 112, an interference signal will only exist when the returned scattered signal is substantially aligned in time with the reference pulse. Since the reference and returned scattered signals have different pulse frequencies, at any given time, this alignment will correspond to only the optical signal scattered from a particular depth in the target.

Thus having a frequency offset between the reference and probe signals has the effect of selectively discriminating in favor of detecting a signal scattered from different depths in the target at different times. This effectively provides an electronic method of scanning in depth (or in the z-axis), with the advantage of having no moving parts. The range of the depth or z-axis scan corresponds to the optical path length of the laser cavity and a full scan occurs with a frequency corresponding to the frequency offset 505.

The optical system 118 in FIG. 1 can then be translated in a direction perpendicular to the z-axis by conventional electromechanical techniques, to provide a two dimensional scan of the target. Translating also in a direction orthogonal to the two dimensional scan provides a three dimensional scan.

The control module 115 in FIG. 1 generates the electronic signals to mode lock both laser diodes 102 and 116 and provides a signal representing the frequency offset between them to the processing module 114. This signal represents the coherence phase offset between the reference and probe signals. This allows the processing module 114 to determine from what depth in the target the detected Interferometric signal was scattered.

The frequency offset between the two pulsed laser sources of the order of 100 Hz, allows for signal integration at different depths and for depth scan rates that are fast compared to typical motion artifacts. This also allows corresponding wavelengths from the sets of wavelengths output by the two pulsed laser sources to have substantially the same wavelength values.

Figure 6:
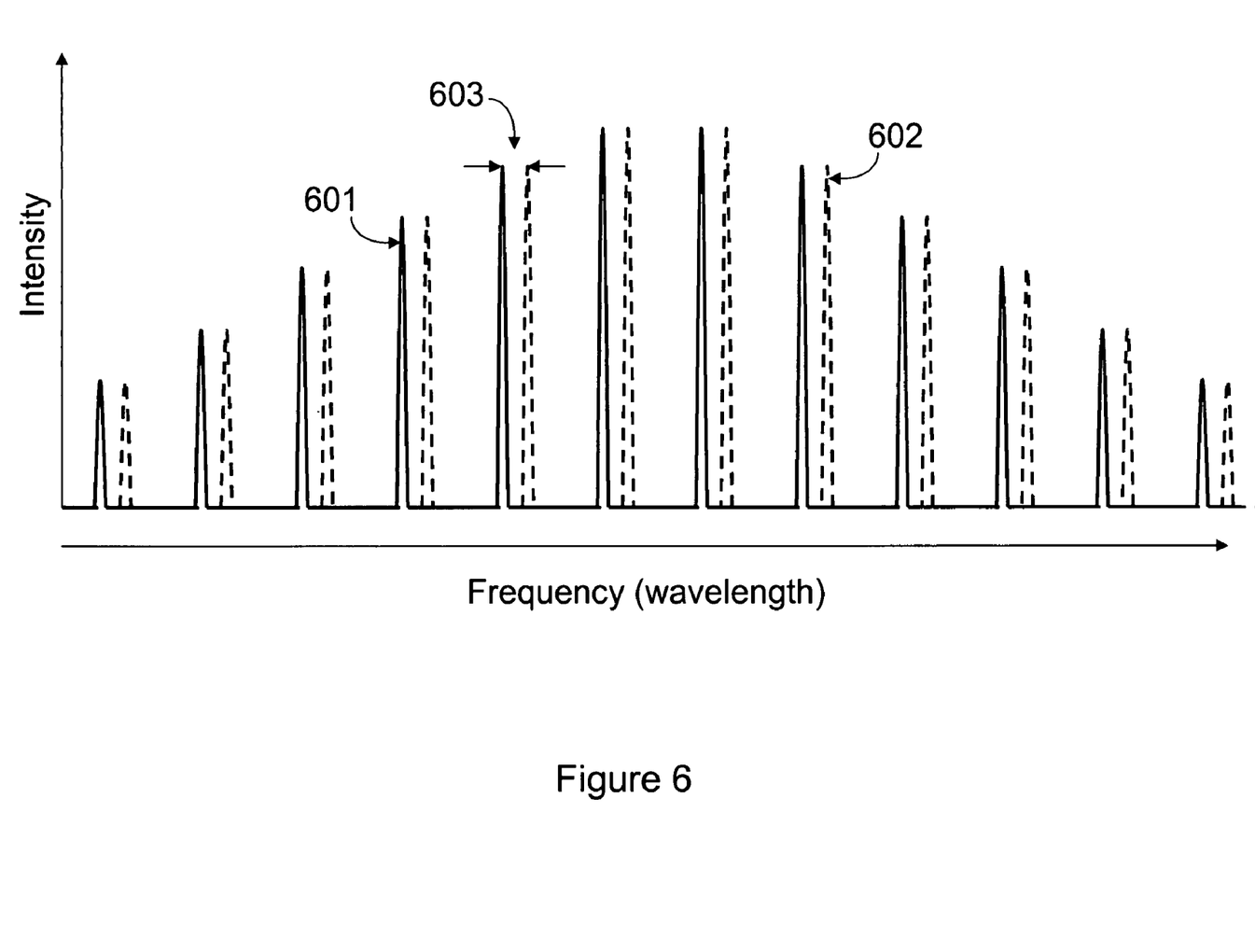
FIG. 6 is a frequency domain illustration of the outputs of two mode locked laser sources.

Alternately, the two wavelength sets can have a frequency offset, that is substantially the same for all corresponding wavelengths from the two sets. In FIG. 6, where the output of two pulsed laser sources are illustrated in the frequency domain and consists of two sets of modes, one mode of one is 601, and one mode of the second is 602. (The second set of modes or wavelengths is illustrated by dashed lines.) These are offset by a frequency offset that is substantially the same for all corresponding modes (or wavelengths) of the two sets. This offset enables more sophisticated signal detection techniques, such as coherent heterodyne techniques.

In alternative embodiments, the pulsed laser sources may consist of gain switched laser diodes, and may include an SOA, or may consist of a Q-switched laser. Spectral broadening may be accomplished by means of non-linear fiber, either in a resonant cavity configuration or in a single pass configuration.

In another alternative embodiment, depth scanning can be accomplished by varying the temporal relationship between the captured scattered signal and the reference signal by modifying the coherence phase offset between the first and second mode locked lasers. This can be done by, for example, having both lasers mode locked at substantially the same frequency and varying the phase relation between RF (radio frequency) signals electronically mode locking the lasers.

Figure 7:
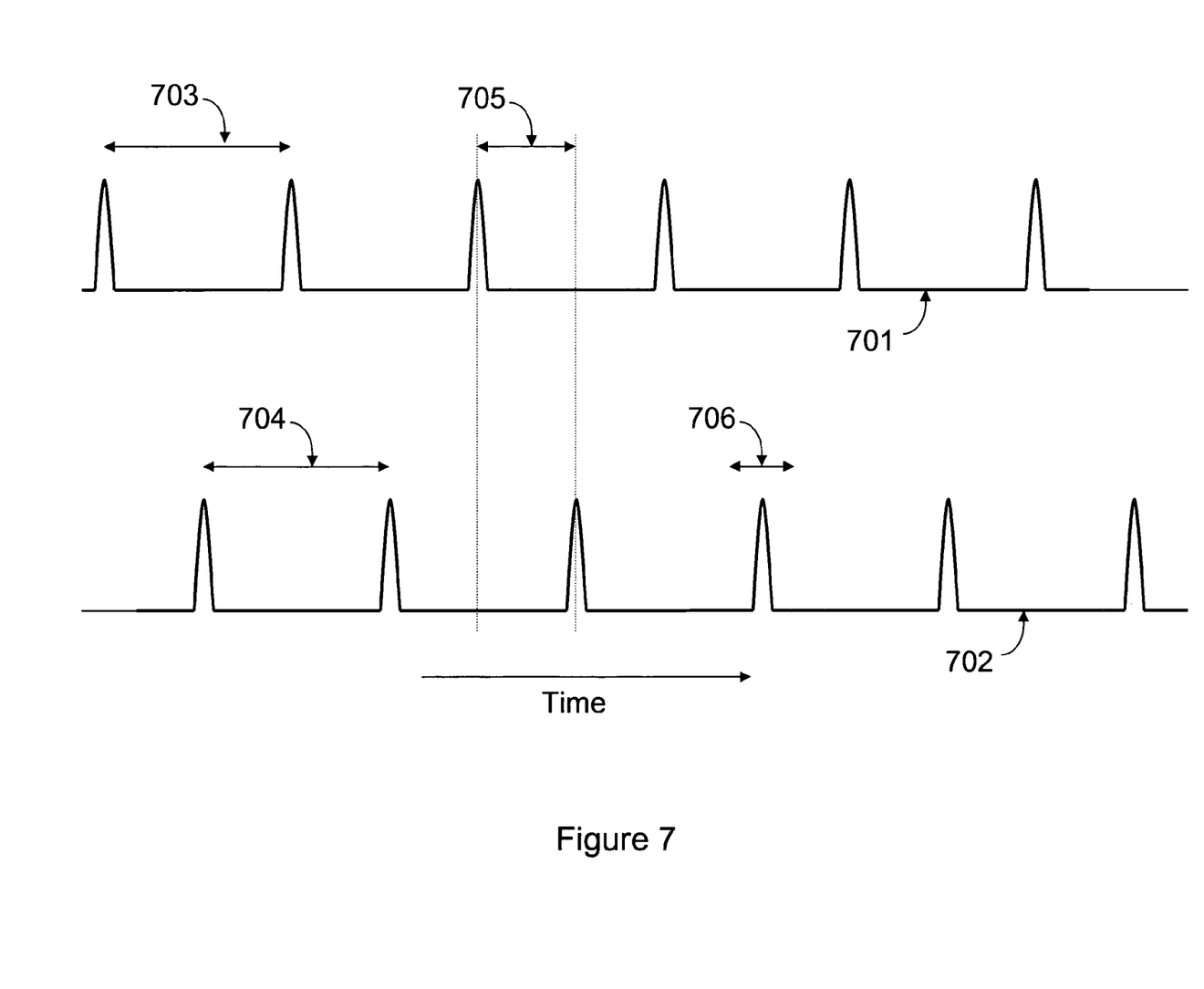
FIG. 7 is a time domain illustration of the outputs of two mode locked laser sources.

Typical outputs of the lasers in such an embodiment are illustrated in FIG. 7, where the first pulsed laser source output 701 and the second pulsed laser source output 702 have substantially the same repetition rate indicated by the periods 703 and 704. The phase coherence offset between the two pulse trains 705 is aligned so the pulse trains are substantially 180 degrees out of phase when the signals are combined interferometrically. The phase relationship can be offset from the 180 degree situation and this offset can be varied.

In this embodiment, the varying phase offset between the first repetitive optical signal and the second repetitive optical signal accomplishes scanning. Scanning is accomplished by varying this phase relationship by an amount, for example, indicated by 706. The scanning frequency is determined by the frequency with which the phase coherence is modulated. The scanning range is determined by the magnitude of the phase coherence variation 706.

The analysis performed on the information acquired by scanning the target can be used to generate a one, two or three dimensional image of the target. Alternately it could be processed to determine the concentration of components of the target, such as analytes, including glucose. The target can be human tissue, such as skin. The control system may also store control parameters and processed information in electronic memory, preferably non-volatile electronic memory.

It is understood that the above description is intended to be illustrative and not restrictive. Many of the features have functional equivalents that are intended to be included in the invention as being taught.

For example, the mode locked laser could be optically pumped, it could be a solid state laser, such as a Cr:LiSAF laser or an Nd doped laser optically pumped by a diode laser and it could be passively mode locked by a Kerr lens or a semiconductor saturable absorber mirror. The pulsed laser source could be a Q-switched micro-chip laser. The system could be a fiber based system, rather than the free space system illustrated. The interferometric detection system could include a second opto electronic detector, detecting the complimentary interference signal to provide differential detection.

Other examples will be apparent to persons skilled in the art. The scope of this invention should therefore not be determined with reference to the above description, but instead should be determined with reference to the appended claims, along with the full scope of equivalents to which such claims are entitled.

What is claimed is:

1. A method for high resolution sub-surface analysis of a target, the method comprising:
   generating a first repetitive optical signal;
   broadening the spectral width of said first repetitive optical signal to form a first broadened optical signal;
   applying at least part of said first broadened optical signal to a target to be analyzed;
   capturing at least part of said first broadened optical signal returned from the target to form a captured returned broadened optical signal which is a returned optical signal;
   generating a second repetitive optical signal;
   broadening the spectral width of said second repetitive optical signal to form a second broadened optical signal which is a reference optical signal;
   combining the returned optical signal with the reference optical signal;
   modifying the coherence phase relationship between the returned optical signal and the reference optical signal;
   detecting an interference signal between the returned optical signal and the reference optical signal;
   processing the detected interference signals at multiple coherence phase relationships;
   performing high resolution analysis of the target; and
   storing the analysis data in non-volatile memory for display, for further analysis, or for future operation of said method.

2. The method of claim 1, wherein a repetitive optical signal is generated by a pulsed laser source.

3. The method of claim 2, wherein the mode locked laser source is a mode locked semiconductor laser.

4. The method of claim 1, wherein broadening of the spectral width is achieved by means of a non linear material.

5. The method of claim 4, wherein the non-linear material comprises a resonant micro ring.

6. The method of claim 4, wherein the non-linear material is contained within the laser cavity.

7. The method of claim 4, wherein the non-linear material is a non-linear fiber.

8. The method of claim 1, wherein part of the first broadened optical signal returned from the target to form a captured returned broadened optical signal is returned due to scattering properties of the target.

9. The method of claim 1, wherein part of the first broadened optical signal returned from the target to form a captured returned broadened optical signal is returned due to discontinuities in the target.

10. The method of claim 9, wherein the discontinuities in the target are caused by changes of refractive index.

11. The method of claim 1, wherein the first repetitive optical signal has a frequency offset from the second repetitive optical signal.

12. The method of claim 1, wherein the first repetitive optical signal has a varying phase offset from the second repetitive optical signal.

13. The method of claim 1, wherein the returned optical signal and the reference optical signal are combined interferometrically.

14. The method of claim 1, wherein the interference signal between the returned optical signal and the reference optical signal is detected by means of at least one opto-electronic detectors.

15. The method of claim 1, wherein the interference signal between the returned optical signal and the reference optical signal is detected, processed and analyzed by an electronic processing system to generate an image of the target to be analyzed.

16. The method of claim 1, wherein the interference signal between the returned optical signal and the reference optical signal is detected, processed and analyzed by an electronic processing system to determine an analyte concentration of the target to be analyzed.

17. A system for high resolution sub-surface analysis of a target comprising:
   a first pulsed light source for generating a first repetitive optical signal;
   a first resonator for broadening the spectral width of said first repetitive optical signal to form a first broadened optical signal;
   a lens for applying at least part of said first broadened optical signal to a target to be analyzed, said lens capturing at least part of said first broadened optical signal returned from the target to form a captured returned broadened optical signal which is a returned optical signal;
   a second pulsed light source for generating a second repetitive optical signal;
   a second resonator for broadening the spectral width of said second repetitive optical signal to form a second broadened optical signal which is a reference optical signal, wherein the resonator also modifies the coherence phase relationship between the returned optical signal and the reference optical signal;

a beamsplitter for combining the returned optical signal with the reference optical signal;

an opto-electronic detector for detecting an interference signal between the returned optical signal and the reference optical signal; and a processor for processing the detected interference signals at multiple coherence phase relationships and performing high resolution analysis of the target; and non-volatile memory for storing the analysis data for display, for further analysis, or for future operation of said system.

18. An apparatus for high resolution sub-surface analysis of a target comprising:

means for generating a first repetitive optical signal;

means for broadening the spectral width of said first repetitive optical signal to form a first broadened optical signal;

means for applying at least part of said first broadened optical signal to a target to be analyzed;

means for capturing at least part of said first broadened optical signal returned from the target to form a captured returned broadened optical signal which is a returned optical signal;

means for generating a second repetitive optical signal;

means for broadening the spectral width of said second repetitive optical signal to form a second broadened optical signal which is a reference optical signal;

means for combining the returned optical signal with the reference optical signal;

means for modifying the coherence phase relationship between the returned optical signal and the reference optical signal;

means for detecting an interference signal between the returned optical signal and the reference optical signal;

means for processing the detected interference signals at multiple coherence phase relationships;

means for performing high resolution analysis of the target; and means for storing the analysis data in non-volatile memory for display, for further analysis, or for future operation of said method.

19. The apparatus of claim 18, wherein a repetitive optical signal is generated by a pulsed laser source.

20. The apparatus of claim 19, wherein the mode locked laser source is a mode locked semiconductor laser.

21. The apparatus of claim 18, wherein broadening of the spectral width is achieved by means of a non linear material.

22. The apparatus of claim 21, wherein the non-linear material comprises a resonant micro ring.

23. The apparatus of claim 21, wherein the non-linear material is contained within the laser cavity.

24. The apparatus of claim 21, wherein the non-linear material is a non-linear fiber.

25. The apparatus of claim 18, wherein part of the first broadened optical signal returned from the target to form a captured returned broadened optical signal is returned due to scattering properties of the target.

26. The apparatus of claim 18, wherein part of the first broadened optical signal returned from the target to form a captured returned broadened optical signal is returned due to discontinuities in the target.

27. The apparatus of claim 26, wherein the discontinuities in the target are caused by changes of refractive index.

28. The apparatus of claim 18, wherein the first repetitive optical signal has a frequency offset from the second repetitive optical signal.

29. The apparatus of claim 18, wherein the first repetitive optical signal has a varying phase offset from the second repetitive optical signal.

30. The apparatus of claim 18, wherein the returned optical signal and the reference optical signal are combined interferometrically.

31. The apparatus of claim 18, wherein the interference signal between the returned optical signal and the reference optical signal is detected by means of at least one opto-electronic detectors.

32. The apparatus of claim 18, wherein the interference signal between the returned optical signal and the reference optical signal is detected, processed and analyzed by an electronic processing system to generate an image of the target to be analyzed.

33. The apparatus of claim 18, wherein the interference signal between the returned optical signal and the reference optical signal is detected, processed and analyzed by an electronic processing system to determine an analyte concentration of the target to be analyzed.

* * * * *